(12) United States Patent
Aiko et al.

(10) Patent No.: US 8,804,109 B2
(45) Date of Patent: *Aug. 12, 2014

(54) DEFECT INSPECTION SYSTEM

(71) Applicant: Hitachi High-Technologies Corporation, Tokyo (JP)

(72) Inventors: Kenji Aiko, Hitachinaka (JP); Shuichi Chikamatsu, Kounosu (JP); Minori Noguchi, Joso (JP); Hisafumi Iwata, Hayama (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/656,353

(22) Filed: Oct. 19, 2012

(65) Prior Publication Data

US 2013/0182100 A1    Jul. 18, 2013

Related U.S. Application Data

(63) Continuation of application No. 12/770,337, filed on Apr. 29, 2010, now Pat. No. 8,319,960, which is a continuation of application No. 12/081,107, filed on Apr. 10, 2008, now Pat. No. 7,733,474.

(30) Foreign Application Priority Data

Apr. 13, 2007    (JP) .................................. 2007-106082

(51) Int. Cl.
*G01N 21/88*    (2006.01)
*G01N 21/95*    (2006.01)
*G01N 21/956*    (2006.01)
*H01L 21/66*    (2006.01)

(52) U.S. Cl.
CPC .......... *G01N 21/9501* (2013.01); *G01N 21/956* (2013.01); *H01L 22/12* (2013.01)
USPC .................................... 356/237.2; 356/237.5

(58) Field of Classification Search
CPC ... G01N 21/9501; G01N 21/94; G01N 21/95; G01N 2021/8825; G01N 21/00; G01N 21/956; H01L 22/12
USPC ............................................ 356/237.1–237.5
See application file for complete search history.

(56) References Cited

U.S. PATENT DOCUMENTS 4,648,696 A * 3/1987 Park et al. ...................... 396/446
5,155,631 A * 10/1992 Snyder et al. .................. 359/708

(Continued)

FOREIGN PATENT DOCUMENTS

JP    01-265220 A    10/1989
JP    10-020211 A    1/1998

(Continued)

OTHER PUBLICATIONS

English translation of Japanese Office Action and abstracts of references cited therein, issued in Japanese Patent Application No. 2007-106082, dated Jul 26, 2012.

(Continued)

*Primary Examiner* — Hoa Pham
(74) *Attorney, Agent, or Firm* — McDermott Will & Emery LLP

(57) ABSTRACT

A defect inspection system can suppress an effect of light from a rough surface or a circuit pattern and increasing a gain of light from a defect to detect the defect with high sensitivity. When a lens with a large NA value is used, the diameter is $10a$, an angle between the sample surface and a traveling direction of the light from a defect being $\alpha 1$. A system receives the light from the defect at a reduced elevation angle $\alpha 2$ with respect to the sample surface to reduce the scattered light, and to increase the light from the defect. The diameter $10a$ is smaller than the diameter $10b$, resulting in a reduction in the ability to focus the scattered light. When a lens having a diameter $10c$ is used, the lens interferes with the sample. To avoid the interference, a portion of the lens interfering with the sample is removed.

6 Claims, 17 Drawing Sheets

(56) References Cited

U.S. PATENT DOCUMENTS

| | | | |
|---|---|---|---|
| D385,899 S | 11/1997 | Murphy et al. | |
| 5,835,475 A * | 11/1998 | Kawakami et al. | 369/112.28 |
| 5,864,394 A | 1/1999 | Jordan, III et al. | |
| 5,991,098 A * | 11/1999 | Pareto | 359/718 |
| 7,304,790 B2 * | 12/2007 | Kawano et al. | 359/383 |
| 7,525,649 B1 | 4/2009 | Leong et al. | |
| 7,733,474 B2 * | 6/2010 | Aiko et al. | 356/237.2 |
| 8,319,960 B2 * | 11/2012 | Aiko et al. | 356/237.2 |
| 2002/0021432 A1 * | 2/2002 | Suzuki et al. | 355/55 |
| 2002/0109101 A1 * | 8/2002 | Hoffmann | 250/458.1 |
| 2005/0122508 A1 | 6/2005 | Uto et al. | |
| 2005/0213086 A1 | 9/2005 | Hamamatsu et al. | |
| 2006/0092643 A1 | 5/2006 | Wong et al. | |
| 2006/0124874 A1 | 6/2006 | Uto et al. | |
| 2006/0132770 A1 | 6/2006 | Girvin et al. | |
| 2006/0290923 A1 | 12/2006 | Nakano et al. | |
| 2008/0059094 A1 | 3/2008 | Shimura et al. | |
| 2008/0291436 A1 | 11/2008 | Aiko et al. | |
| 2008/0291439 A1 | 11/2008 | Sones et al. | |
| 2008/0304055 A1 | 12/2008 | Oshima et al. | |
| 2009/0179142 A1 | 7/2009 | Duparre et al. | |

FOREIGN PATENT DOCUMENTS

| | | |
|---|---|---|
| JP | 2004-093252 A | 3/2004 |
| JP | 2004-177284 A | 6/2004 |
| JP | 3566589 | 6/2004 |
| JP | 2005-156537 A | 6/2005 |
| JP | 2005-283190 A | 10/2005 |
| JP | 2006-017630 A | 1/2006 |
| JP | 2006-098154 A | 4/2006 |
| JP | 2006-162500 A | 6/2006 |
| JP | 2006-201179 A | 8/2006 |
| JP | 2007-302997 A | 11/2007 |

OTHER PUBLICATIONS

Entire Prosecution of U.S. Appl. No. 12/770,337, to Kenji Aiko, filed Apr. 29, 2010, entitled "Defect Inspection System."

Entire Prosecution of U.S. Appl. No. 12/081,107, to Kenji Aiko, filed Apr. 10, 2008, entitled "Defect Inspection System."

Japanese Office Action issued in Japanese Patent Application 2012-138409 dated Apr. 23, 2013 with English Translation.

* cited by examiner

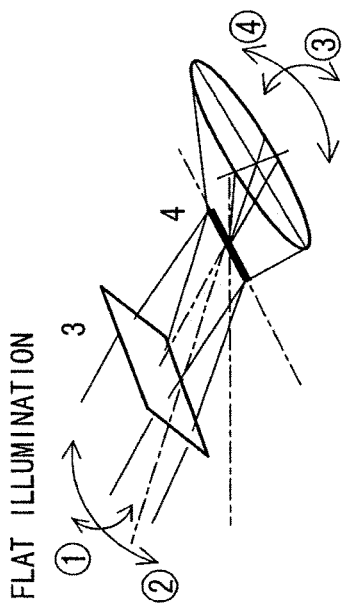

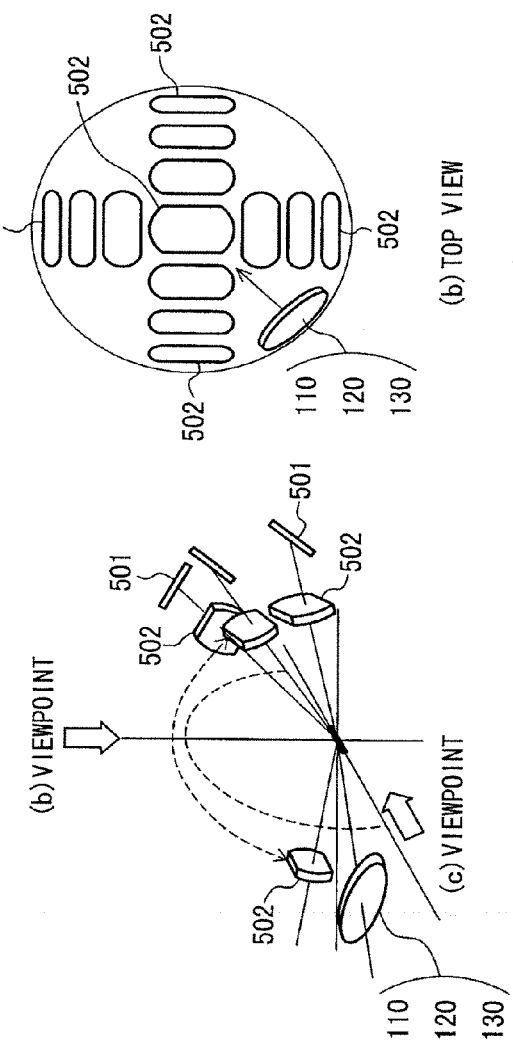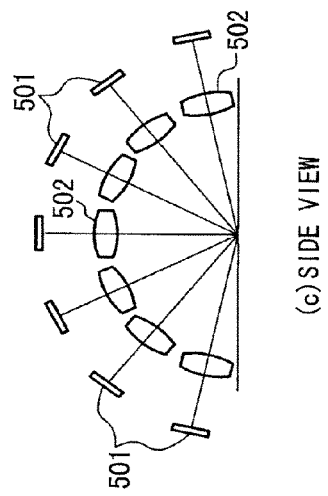

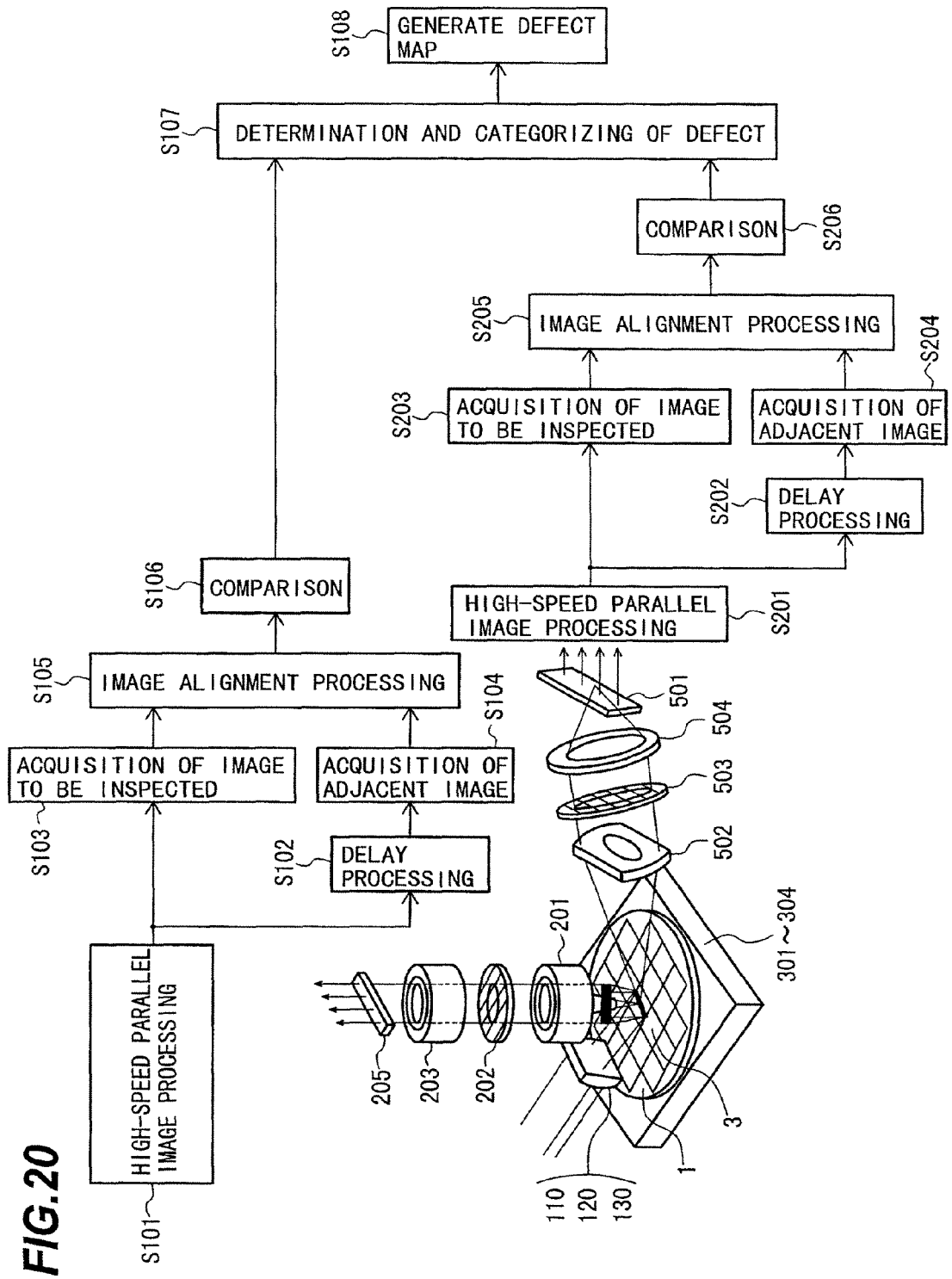

ial or a defect. It is
DEFECT INSPECTION SYSTEM

RELATED APPLICATIONS

This application is a Continuation of U.S. application Ser. No. 12/770,337, filed Apr. 29, 2010, which is a Continuation of U.S. application Ser. No. 12/081,107, filed on Apr. 10, 2008, now U.S. Pat. No. 7,733,474, claiming priority of Japanese Patent Application No. 2007-106082, filed on Apr. 13, 2007, of which the entire contents of each are hereby incorporated by reference.

BACKGROUND OF THE INVENTION

1. Field of the Invention

The present invention relates to a defect inspection system for detecting a foreign material and a defect produced in a process for manufacturing a large scale integration (LSI) semiconductor device or a flat display substrate.

2. Description of the Related Art

In the process for manufacturing a semiconductor LSI, for example, a foreign material or a defect pattern present on a substrate (wafer) may cause a malfunction such as a short circuit and insulation. With the tendency of reducing the size of a semiconductor element, a micro foreign material and a defect pattern cannot be ignored as the cause of the malfunction. Therefore, the importance of the following technique is increased: a technique for inspecting a foreign material and a defect during the process for manufacturing a semiconductor wafer and for managing the yield in order to take measures for reducing defects.

Defect inspection techniques are mainly divided into two methods, a bright field imaging method and a dark field imaging method. The bright field imaging method is to illuminate a sample and detect light (zero-order diffracted light) specularly reflected from the sample, while the dark field imaging method is to detect scattered light, without detecting the light (zero-order diffracted light) specularly reflected from the sample.

Each of JP-A-2005-283190 and Japanese Patent No. 3566589 discloses a technique using the dark field imaging method. JP-A-2005-283190 describes a technique for using a plurality of illumination sections and switching between light paths of the illumination sections based on the type of a foreign material or a defect. Japanese Patent No. 3566589 describes a technique for illuminating a sample substrate having a circuit pattern formed thereon with beams substantially parallel to each other in a longitudinal direction of an elongated beam spot formed by the beams, the beams propagating in a direction corresponding to a predetermined angle with respect to a normal to the substrate, a predetermined angle with respect to main straight lines of the circuit pattern and a substantial right angle with respect to the direction of scanning the sample substrate mounted on a stage.

SUMMARY OF THE INVENTION

The defect inspection technique using the dark field imaging method is to improve inspection sensitivity by receiving a large amount of signals output from a defect to be scanned and to suppress signals output from other parts such as a regular circuit pattern on the surface of a substrate.

The principle of a dark field imaging method related to the present invention will be clarified. First, a sample is opaque to an illumination light beam. The illumination light beam incident on the sample is specularly reflected, diffracted, or scattered (above the sample (in an upper hemisphere)) on the surface of the sample, or a foreign material or a defect. It is preferable that light derived from the foreign material or the defect be detected and that light derived from other parts such as a regular circuit pattern on the surface of the substrate be not detected. To achieve this preferable configuration, the incident direction (defined by an elevation angle formed between the direction of traveling of the illumination light beam and the surface of a sample and an azimuth angle formed between the direction of traveling of the illumination light beam and a specified direction) of the illumination light beam is specified, and the receiving direction (defined by an elevation angle formed between the direction of traveling of light scattered from the sample and the surface of sample and an azimuth angle formed between the direction of traveling of the light scattered from the sample and the specified direction) of light to be received by a detection system is determined. The incident direction of the illumination light beam and the receiving direction of light to be received by the detection system in the upper hemisphere characterize defect inspection techniques provided in respective optics systems.

An actual defect inspection system encounters problems in the abovementioned principle and in the mechanical configuration of an optics system. In other words, it is necessary that a limitation of an installation space be considered.

Regarding conventional techniques, an optical lens (objective lens) for receiving light, which is shown in FIGS. 12 and 13 of Japanese Patent No. 3566589, has a circular shape. The circular lens is provided in a casing (refer to FIG. 1 of JP-A-2005-283190). This causes a limitation of an installation space, causing difficulty in improvement of inspection sensitivity.

To avoid the above problem, a technique for covering the entire surface of the upper hemisphere with a small-diameter fiber can be considered. This technique, however, causes the configuration of the system to be complicated, and has not been put into practical use yet.

It is, therefore an object of the present invention to provide a defect inspection system capable of detecting a defect and the like present on the surface of a sample with high sensitivity by suppressing an effect of light scattered from a rough surface of the sample and a regular circuit pattern and increasing a gain of the light scattered from a defect or a foreign material.

According to the present invention, an optical lens is arranged between a sample to be inspected and detection unit for detecting light scattered from the surface of a sample which is irradiated with an illumination light beam. The optical lens focuses the scattered light on the detection unit. The length in the azimuth direction is made larger than the length in the elevation direction with respect to the surface of the sample to be inspected The defect inspection system according to the present invention is capable of suppressing an effect of light scattered from a rough surface of the sample to be inspected and a regular circuit pattern and increasing a gain of the light scattered from a defect and a foreign material to detect a defect and the like present on the surface of a sample with high sensitivity.

BRIEF DESCRIPTION OF THE DRAWINGS

FIG. 9 is a diagram explaining the effect of the present invention.

FIGS. 10A to 10C are each a diagram showing a modification of an embodiment of the present invention.

FIG. 20 is a diagram showing an example of a modification of the optics system for detection of light scattered at a right angle and almost right angle, as shown in FIG. 19.

DETAILED DESCRIPTION OF THE PREFERRED EMBODIMENTS

An embodiment of the present invention will be described with reference to the accompanying drawings.

Figure 1A:
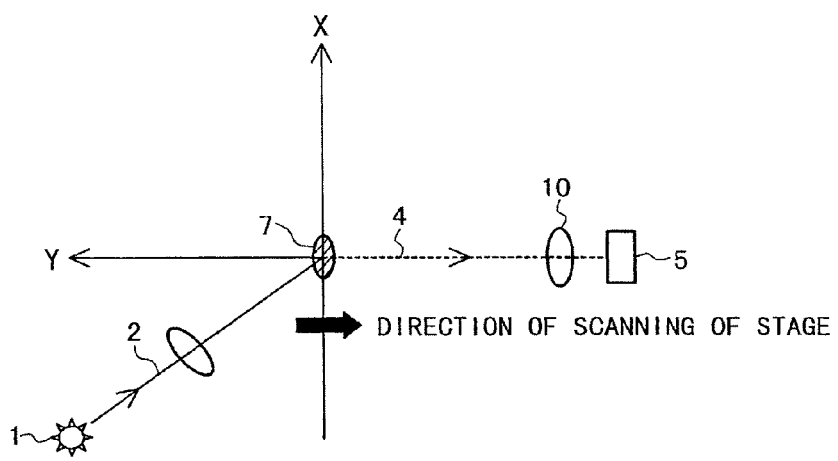
FIG. 1A is a top view of an optics system for detection, explaining the principle of the present invention.
Figure 1B:
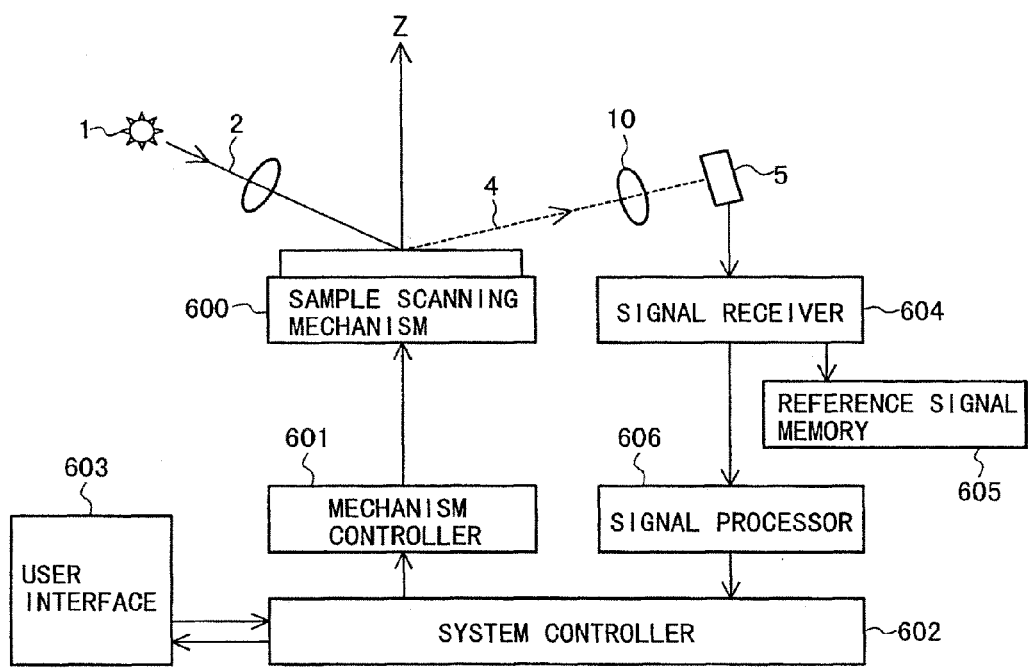
FIG. 1B is a diagram showing the configuration of the optics system for detection, explaining the principle of the present invention.

First, the principle of the present invention will be described. FIG. 1A is a top view of an optics system (hereinafter referred to as a "detection optics system") for detection of light. FIG. 1B is a diagram showing the configuration of a system for efficiently detecting a distribution of light scattered from a defect present on a silicon wafer. In FIGS. 1A and 1B, a wafer to be inspected is placed on a sample scanning mechanism 600, and is illuminated by an optics system for illumination with an illumination beam 2 from an oblique direction with respect to the surface of the silicon wafer. The optics system has an optical source 1. The illumination beam 2 is distributed on the silicon wafer to form, on the silicon wafer, a beam spot having an elongated shape with a longer axis perpendicular to a direction of scanning of a stage. If a defect is present on the silicon wafer, the light 4 scattered from the defect is received by an optics system (a lens 10) for detection. The detection optics system is arranged at a position to ensure that an imaginary line extending between the center of the lens 10 and the center of a beam spot is inclined with respect to the surface of the silicon wafer. An optical image obtained by the detection optics system is converted into an electrical signal by a photoelectric converter 5. A part of the electrical signal is transmitted through a signal receiver 604 directly to a signal processor 606, and processed by the signal processor 606. The remaining part of the electrical signal is transmitted through a reference signal memory 605 to the signal processor 606. The signal processor 606 is designed to detect a defect, determine whether the defect is true or false, classify the type of the defect, and determine the shape of the defect.

A system controller 602 controls a series of the signal processing, operations for the abovementioned determinations, a command to a mechanism controller 601, and transmission and reception of a signal from and to a user interface 603.

Figure 2A:
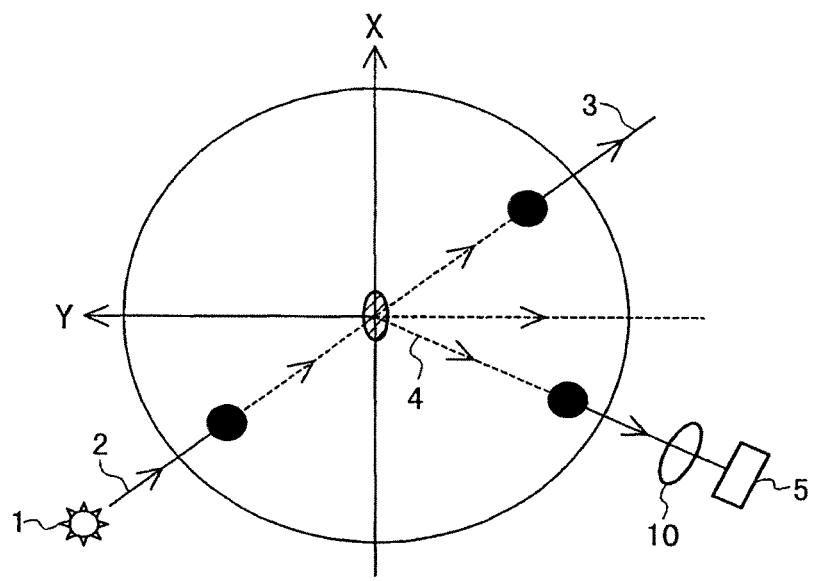
FIGS. 2A and 2B are each a diagram showing the positional relationship between the optics system for detection and an optics system for illumination, explaining the principle of the present invention.
Figure 2B:
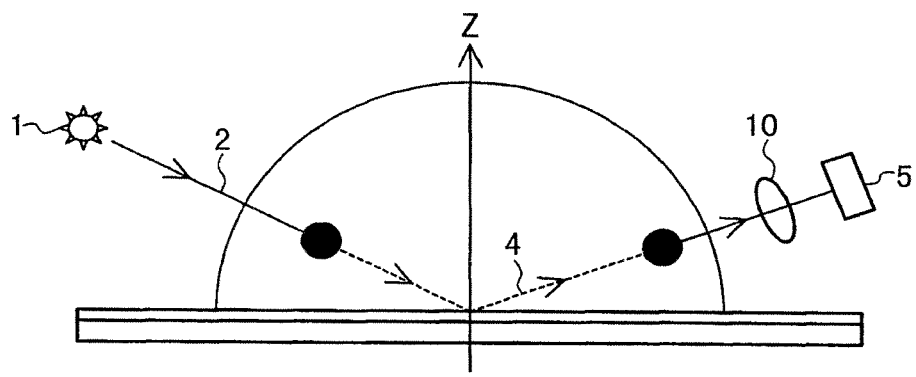

Next, FIGS. 2A and 2B are each a diagram explaining the positional relationship between an optics system for illumination and the detection optics system. In FIG. 2A, an optical source 1 drawn on the left bottom side of FIG. 2A emits an illumination light beam 2. In this case, the illumination light beam is specularly reflected on the wafer to form light 3, which travels in a direction on the right top side of FIG. 2A. The optics system (hereinafter referred to as the "oblique detection optics system") for detection of light scattered at an acute angle with respect to the surface of the sample can be installed in any azimuth direction with respect to the center of the beam spot formed on the wafer (in a horizontal direction with respect to the surface of the wafer) to ensure that the specularly reflected light 3 is not received by the oblique detection optics system. FIG. 2B is a side view of the arrangement with the optics system for illumination and the detection optics system. The following two angles can be adjusted: the incident angle (elevation angle) of scattered light 4 emitted by the optics system for illumination with respect to the surface of the wafer; and the output angle (elevation angle) of the scattered light 4 with respect to the surface of the wafer. To detect a defect with high sensitivity, the value of the elevation angle is set to be low since a signal with a high signal-to-noise ratio is detected from the defect.

Figure 3A:
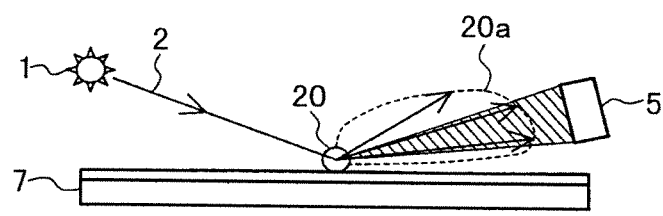
FIGS. 3A to 3C are each a diagram showing characteristics of distribution of light reflected on and scattered from a defect and a back surface of a thin film, explaining the principle of the present invention.
Figure 3B:
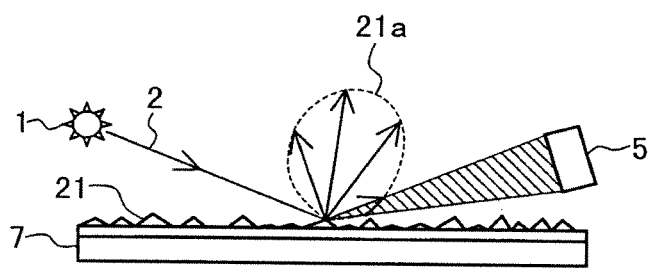
Figure 3C:
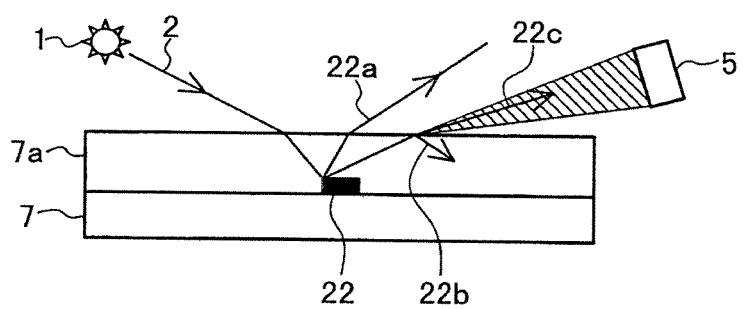

FIGS. 3A to 3C are diagrams each showing a distribution of light scattered from a rough surface of a wafer. In FIG. 3A, the surface of a wafer 7 is illuminated with the illumination light beam 2 from an oblique direction, and light 20a scattered from a defect 20 is intensively distributed into a space, which is similar to a space of the distribution of the illumination light beam 2 specularly reflected. As shown in FIG. 3B, light 21a is scattered from a rough surface 21 (regular portion) of the wafer 7, such as grains, and is relatively widely distributed. The amount of components of the light 21a directing to a detector 5 is small.

Thus, the detector 5 is installed to ensure that the optics system detects the light scattered at a low elevation angle with respect to the surface of the wafer 7, resulting in the fact that the amount of the light scattered from the rough surface of the wafer 7 is small and the oblique detection optics system effectively receives a signal from the defect. As shown in FIG. 3C, if the surface of the wafer 7 is covered with a transparent oxide film, the amount of light 22c reflected from the defect 22 at a low elevation angle with respect to the surface of the wafer 7 is smaller than that of light 22a reflected from the defect 22 at a high elevation angle with respect to the surface of the wafer 7 at an interface 7a of the oxide film due to reflectivity of the surface of the oxide film and distribution of transmissivity (since light 22b reflected from the defect 22 is separated from the light 22c). In this case, it is necessary that the detector 5 be installed in the vicinity of the wafer 7 to receive light reflected from the defect 22 at a low elevation angle with respect to the surface of the wafer 7 since the detector 5 detects a signal coming from the defect 22 on a bottom surface of the oxide film with high sensitivity and with low susceptibility to light scattered from the rough bottom surface of the transparent oxide film 7a or a circuit pattern.

Figure 4A:
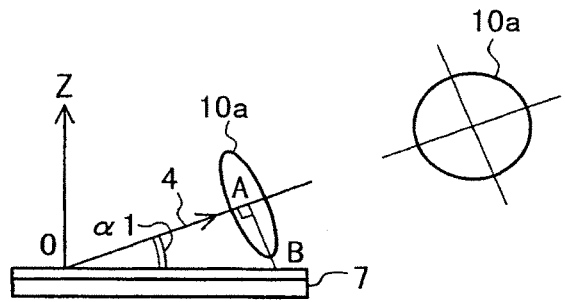
FIGS. 4A to 4E are each a diagram showing the relationship between an aperture of the lens for detection and an elevation angle of an optical lens for detecting in oblique direction.
Figure 4B:
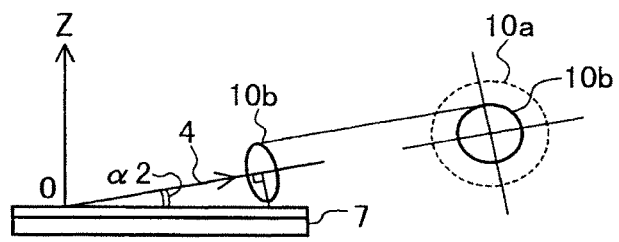

FIGS. 4A to 4e each show the configuration of the detection optics system in the case of detection of light scattered at an acute angle with respect to the surface of the wafer 7. If the detection optics system detects light with high sensitivity, an angle of an aperture for receiving light from a lens needs to be large. FIG. 4A shows an optics system with a lens having a large numerical aperture (NA). In FIG. 4, the outer diameter of the lens is a value of 10a, and an angle formed between the surface of the wafer 7 and a direction of traveling of the light 4 is a value of α1. FIG. 4B shows the case where the oblique detection optics system receives the light 4 reflected from the defect at a reduced elevation angle α2 with respect to the surface of the wafer 7 to reduce light scattered from a rough surface of the wafer 7, a rough bottom surface of the oxide film, and a circuit pattern, and to increase the amount of the light, which is scattered from the defect and is to be detected. In this case, the elevation angle α2 can be set to be smaller than the elevation angle α1. The outer diameter 10b of the lens, however, is smaller than the outer diameter 10a of the lens. As a result, the lens having the outer diameter 10b has a lower ability to focus the scattered light than that of the lens having the outer diameter 10a.

Figure 4C:
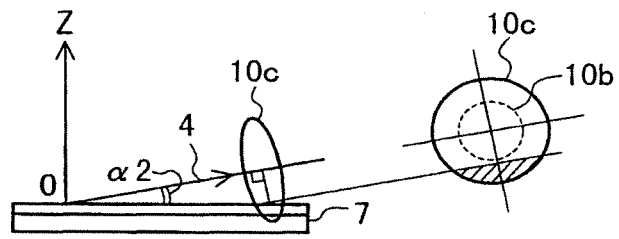

If the lens shown in FIG. 4C has an outer diameter 10c similar to the outer diameter 10a shown in FIG. 4A to increase the ability to focus the scattered light, the lens interferes with the wafer 7.

Figure 4D:
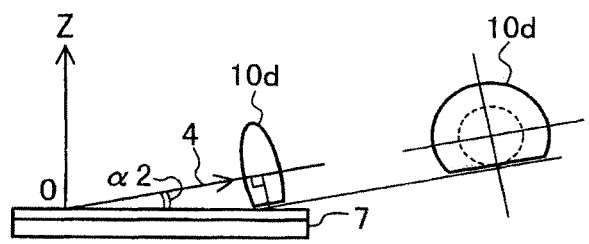
Figure 4E:
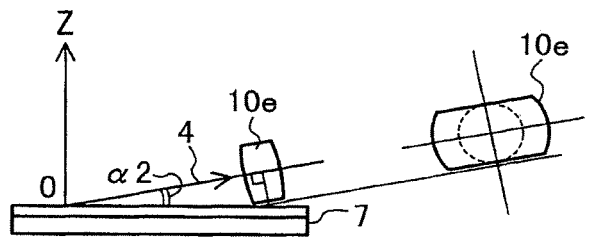

To avoid the interference, a portion of the lens, which interferences with the wafer 7, is removed. The lens with the portion removed is shown in FIGS. 4D and 4E. The removal of the portion which interferences with the wafer 7 allows the lens to have an aperture larger than that of the lens having the outer diameter 10b while the elevation angle α2 is maintained. This makes it possible to improve the ability to detect the scattered light and performance of the lens simultaneously. In FIG. 4E, a portion of the lens shown in FIG. 4D, which is located on the opposite side of the removed portion, is removed to form an adjusted elliptical lens. The adjusted elliptical lens shown in FIG. 4E can reduce its volume in an elevation direction parallel to a normal to the direction of traveling of the light 4 reflected from the sample at the elevation angle α2. The adjusted elliptical lens allows the oblique detection optics system with high lens performance to be installed. The optics system is also assembled with high density implementation in an elevation direction. A plurality of the oblique detection optics systems makes it possible to increase information to be detected from a defect, resulting in the fact that the ability to detect the defect and the ability to classify the type of the defect can be improved.

Next, a description will be made of the definition of the shape of the adjusted elliptical lens. The adjusted elliptical lens has a shape obtained by cutting a circular lens by use of two cutting lines parallel to each other. The adjusted elliptical lens has two straight sides parallel to each other and two elliptical arcs located symmetrically to a central axis thereof, which is perpendicular to the two straight sides. The distance between the two straight sides is smaller than the maximum length of an imaginary line extending between the two elliptical arcs, the imaginary line being parallel to the two straight sides.

As examples of values of the optics system, the NA in an elevation direction (parallel to a normal to the direction of traveling of the light, which is scattered from the sample and is to be detected by the optics system) can be 0.12, the NA in an azimuth direction (parallel to the surface of the sample) can be 0.45, and the elevation angle can be 12 degrees.

Figure 5A:
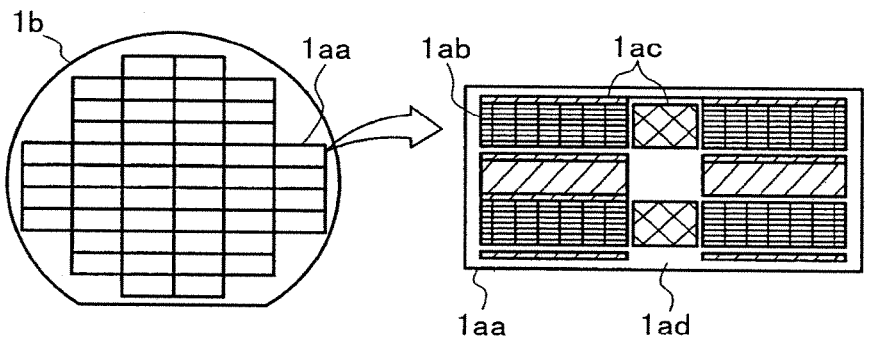
FIGS. 5A and 5B are each a diagram showing a semiconductor wafer with LSI arranged thereon, which is an inspection sample of the present invention.

Next, with reference to FIGS. 5A and 5B, a description will be made of a sample to be inspected by a defect inspection system according to the present invention. A semiconductor wafer 1a shown in FIG. 5A has chips 1aa two-dimensionally arranged at a predetermined interval. Each of the chips 1aa is composed of a memory LSI. Each of the chips 1aa mainly includes: a memory cell area 1ab; a peripheral circuit area 1ac composed of a decoder, a control circuit and the like; and another area 1ad. The memory cell area 1ab has a repetitive memory cell pattern with memory cells regularly arranged in a two-dimensional manner. The peripheral circuit area 1ac has a non-repetitive pattern with circuits irregularly arranged in a two-dimensional manner.

Figure 5B:
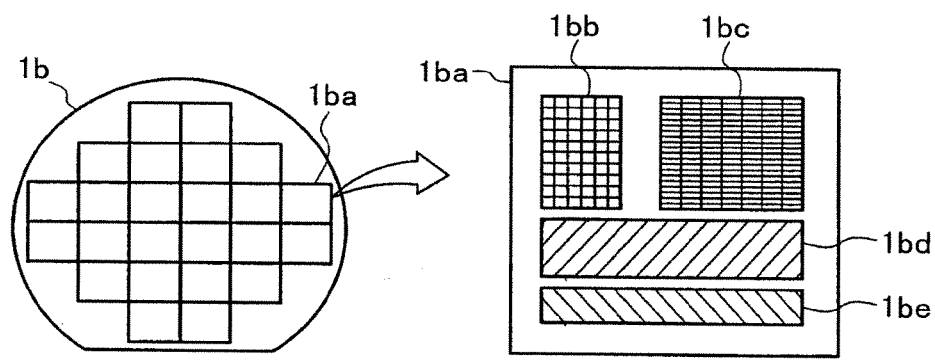

A semiconductor wafer 1b shown in FIG. 5B has chips 1ba, each of which is composed of LSIs such as microcomputers two-dimensionally arranged at a predetermined interval. Each of the chips 1ba mainly includes: a register area 1bb, a memory area 1bc, a central processing unit (CPU) core area 1bd, and an input/output area 1be. FIG. 5B is a conceptual diagram showing the arrangement including the memory area 1bc, the CPU core area 1bd and the input/output area 1be. The register area 1bb has a repetitive pattern with registers regularly arranged in a two-dimensional manner, and the memory area 1bc has a repetitive pattern with memories regularly arranged in a two-dimensional manner. The CPU core area 1bd has a non-repetitive pattern with CPU cores irregularly arranged, and the input/output area 1be has a non-repetitive pattern with input/output sections irregularly arranged. As described above, the samples 1 to be inspected by the defect inspection system according to the present invention, which are the semiconductor wafers 1a and 1b shown in FIGS. 5A and 5B respectively, have chips regularly arranged. In each of the chips, the minimum line width varies depending on the area. Also, some of the areas each have a repetitive pattern and the remaining areas each have a non-repetitive pattern. Various configurations can be considered depending on the areas.

Next, a description will be made of effects of the oblique detection optics system using the adjusted elliptical lens shown in FIG. 4D and the oblique detection optics system using the adjusted elliptical lens shown in FIG. 4E when the sample shown in FIG. 5A or the sample shown in FIG. 5B is used.

Effect 1

Figure 6:
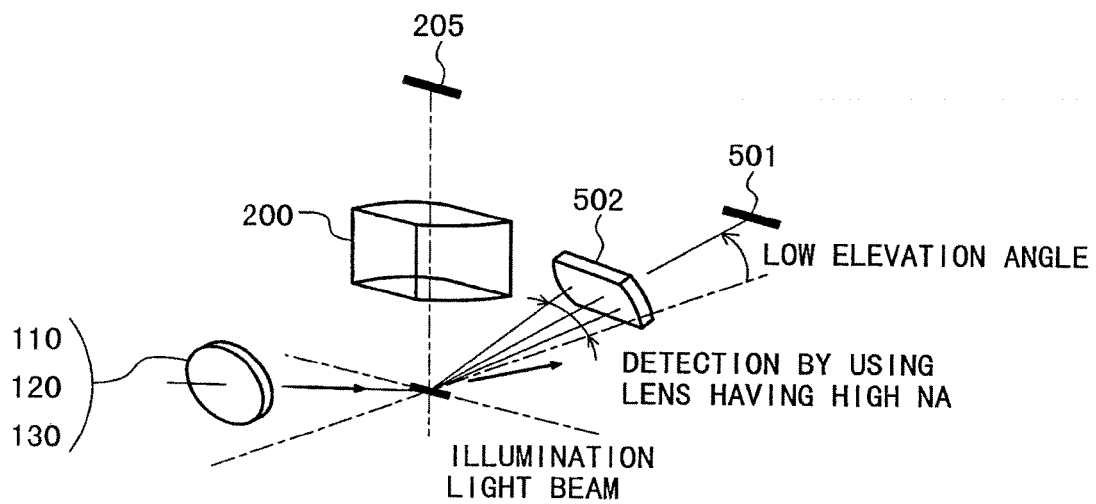
FIG. 6 is a diagram explaining an effect of the present invention.

It is possible to install the oblique detection optics system with a high numerical aperture (aperture ratio) at a position corresponding to a low elevation angle formed between the direction of traveling of light scattered from the sample and the surface of the sample. As shown in FIG. 6, the oblique detection optics system is configured to ensure that the sample is illuminated with light through illumination lenses 110, 120 and 130 and that a detector 501 detects light scattered from the sample through an adjusted elliptical lens 502. In the oblique detection optics system, an aperture angle of the adjusted elliptical lens can be large in the horizontal direction (parallel to the surface of the sample) to improve the optical performance.

Figure 7A:
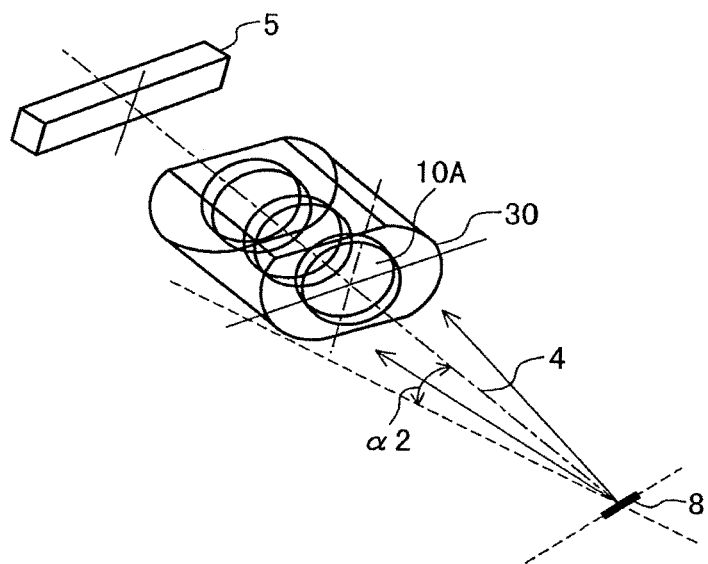
FIGS. 7A and 7B are each a diagram explaining a difference in effect between an adjusted elliptical lens according to the present invention and a circular lens.
Figure 7B:
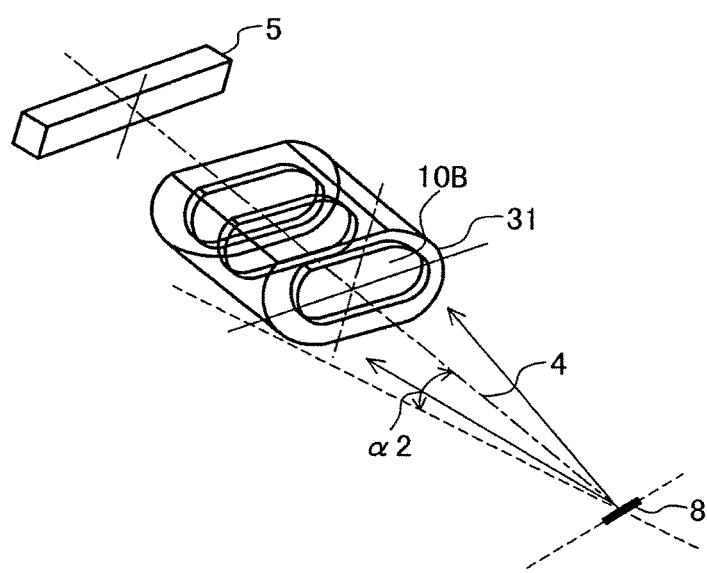

With reference to FIGS. 7A and 7B, a circular lens 10A mounted in a casing 30 and an elliptical lens 10B mounted in a casing 31 are compared with each other. If an elevation angle is α2 in FIGS. 7A and 7B, the aperture angle of the elliptical lens 10B can be larger than that of the circular lens 10A in the horizontal direction.

Effect 2

It is possible to detect a high signal-to-noise ratio since the numerical aperture is determined based on the difference between characteristics of the scattered light.

Returning back to FIGS. 3A to 3C, it is understood that, in the case where the sample is illuminated with the light beam from the oblique direction, and light scattered from the sample is detected in a direction other than the direction of traveling of the specularly reflected light, the ability to detect the light can be improved by reducing the aperture angle in the elevation direction to reduce background noise caused by irregular grains and increasing the aperture angle in the azimuth direction to increase the amount of the light scattered from the defect. It is, therefore, understood that the adjusted elliptical lens is optimal to detect the scattered light with high sensitivity.

The above description was made of the oblique detection optics system in which the light reflected at a low elevation angle with respect to the surface of the sample is detected. However, it has been reported that it is effective to detect a defect present on a part of a pattern by using the optics system for irradiating the illumination light beam at a high elevation angle with respect to the surface of the sample, and the optics system (hereinafter referred to as the "upward detection optics system) for detection of light scattered upwardly with respect to the surface of the sample. In this case, it is possible to improve the ability to detect the scattered light by using the adjusted elliptical lens of the upward detection optics system and by adjusting aperture angles in two directions perpendicular to each other.

In order to obtain the abovementioned effects, the adjusted elliptical lens can be provided only in the upward detection optics system.

Effect 3

It is possible to achieve a detection optics system, which is assembled with high density implementation by using a flat optical lens for detection.

Figure 8:
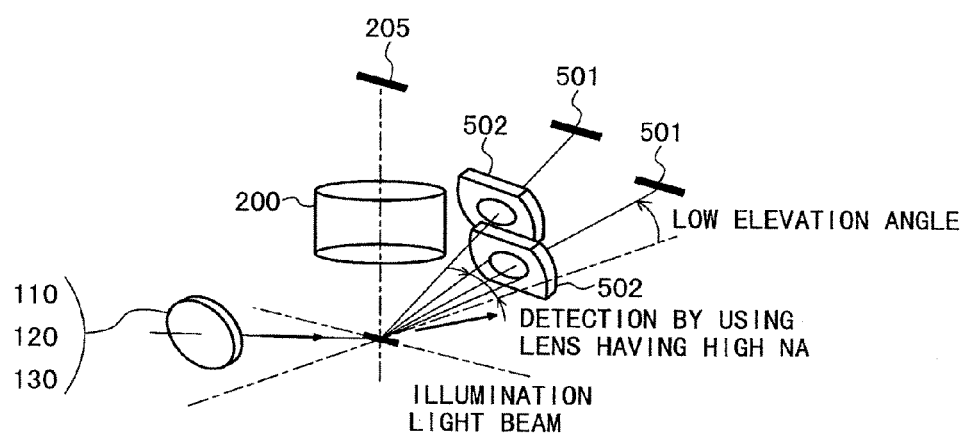
FIG. 8 is a diagram showing an example of an arrangement in which a plurality of the adjusted elliptical lenses are provided at positions corresponding to elevation angles different from each other, explaining the effect of present invention.

The adjusted elliptical lens with a small aperture angle in the elevation direction and a large aperture angle in the azimuth direction can be installed in a small space in the elevation direction. As shown in FIG. 8, a plurality of the adjusted elliptical lenses 502 can be provided with high density implementation in the elevation direction and with a small gap between the adjusted elliptical lenses. The detection optics system can be arranged with high density implementation in the elevation direction and at an optimal elevation angle appropriate for characteristics of light scattered from the defect. The detection optics system is capable of detecting the defect with high efficiency. In addition, this arrangement makes it possible for the optics system to detect a small or minute defect with detection ability improved. Furthermore, the arrangement makes it possible to install a plurality of the detectors to categorize defects. The method for categorizing defects will be described in Effect 4.

Effect 4

It is possible to discriminate scattering characteristics and categorize defects by using the plurality of detectors.

The light scattered from the defect varies in elevation angle, at which the scattered light is reflected, depending on the type of the defect. The types of the defects include an attached foreign material, a scratch, a short circuit occurring in a circuit pattern, a disconnection occurring in a circuit pattern, and a pit. Although it is necessary to detect and categorize such defects, the directions of light scattered from such defects may be different depending on the type of the defect. For example, as shown in FIGS. 10A to 10C, three or more of the adjusted elliptical lenses 502 are installed at positions defined by the same azimuth directions and elevation directions different from each other, or at positions defined by the same elevation direction and azimuth directions different from each other, or at positions defined by azimuth directions different from each other and elevation directions different from each other to achieve an oblique detection optics system 503 with high density implementation. The oblique detection optics system 503 is adapted to detect light scattered from a defect present on the sample at an acute angle with the surface of the sample. The plurality of detectors 501 are capable of detecting light scattered from the defect. This makes it possible to determine a direction of traveling of the light scattered at a low elevation angle and at a high elevation angle and to categorize the defect based on the direction of the scattered light. In addition, the direction of the scattered light to be detected varies depending on the direction of the illumination light beam, resulting in the fact that information on the categories can be increased.

Figure 11A:
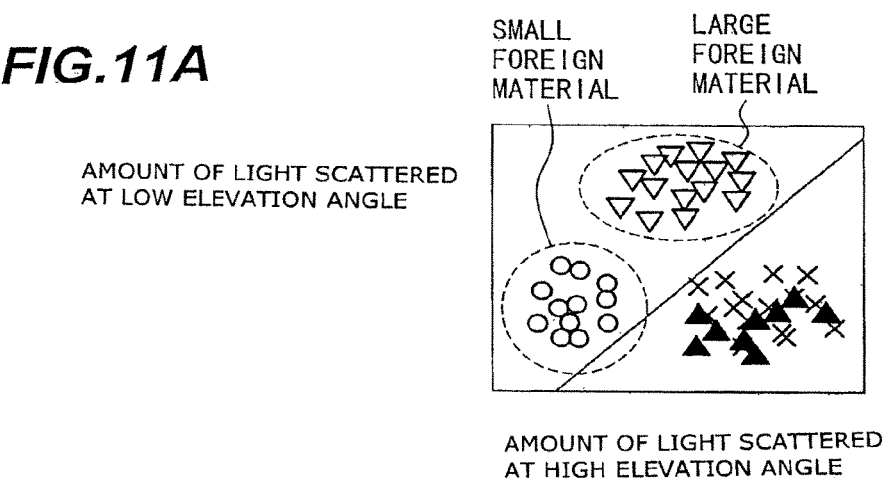
FIGS. 11A to 11C are each a diagram explaining a difference in defect accumulation between illumination at a low elevation angle with respect to the surface of the sample and illumination at a high elevation angle with respect to the surface of the sample.
Figure 11B:
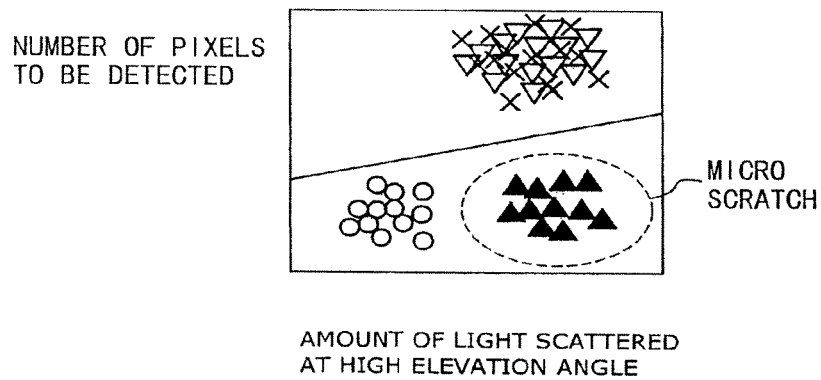
Figure 11C:
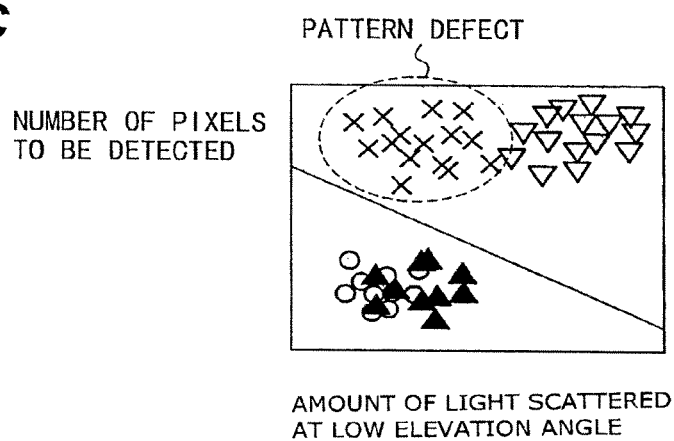

FIGS. 11A to 11C are diagrams to compare a case example in which a sample is detected by using light incident on the sample at a high elevation angle with respect to the surface of the sample, with a case example in which a sample is detected by using light incident on the sample at a low elevation angle with respect to the surface of the sample. As shown in FIGS. 11A to 11C, it is understood that the types of the defects can be discriminated based on the elevation angle of the illumination light beam with respect to the surface of the sample, an azimuth angle of the detected light with respect to a specified direction, and the elevation angle of the detected light with respect to the surface of the sample. A polarization state of the light to illuminate the defect is selected from among S-polarized light, P-polarized light, circularly-polarized light, and non-polarized light to ensure that a condition for spatial distribution of the scattered light is varied. By using the polarization condition, the ability to estimate the type of the detected defect can be improved. The plurality of detectors provide a great effect to improve the ability to categorize the defect.

Effect 5

An anisotropic aperture of the detection optics system is advantageous based on conditions for illumination performed by the optics system for illumination to form a beam.

Here, a beam to be formed by the detection optics system is compared with the beam to be formed by the optics system for illumination. As shown in FIG. 9, in the detection optics system, an elongated beam spot of the illumination light beam is formed without the illumination light beam being focused, the length of the illumination light beam being perpendicular to the direction of scanning of the stage. The illumination light beam is focused to concentrate on illumination power in the direction (the elevation direction) perpendicular to the direction of scanning of the stage. That is, the illumination light beam is incident on the surface of the wafer at an elevation angle with respect to the surface of the wafer in order to inspect the wafer. In the case where the light is reflected on the wafer to be inspected, an aperture angle in the azimuth direction (horizontal direction is required to be large for the lens of the detection optics system as a condition necessary for detecting a defect (since the illumination light is parallel light). However, it is not necessary that an aperture angle in the elevation direction be large for the lens of the detection optics system. In the case of using the adjusted elliptical lens, the condition for the aperture matches with the condition for the beam formation performed by the optics system for illumination, and it is necessary that the aperture of the detection optics system be based on the numerical aperture (NA) of the optics system for beam formation, which is provided in the optics system for illumination, resulting in the fact that the optics system can detect a defect with high efficiency.

Figure 12:
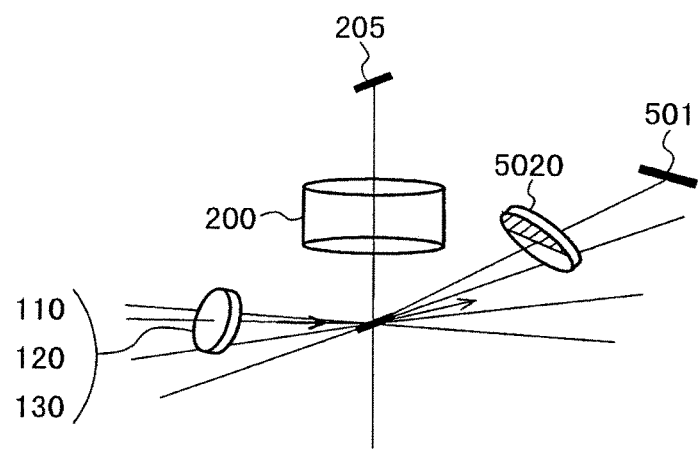
FIG. 12 is a diagram showing an example of a modification of the present invention.

It should be noted that use of some of the aperture angles of the detection optics system makes it possible to efficiently detect a defect. The detection optics system is installed to obtain aperture angles in two directions perpendicular to each other and is capable of detecting a defect with high efficiency even if a part of the detection optics system having a circular lens with an isotropic aperture is used to change the aperture angle. As shown in FIG. 12, when the scattered light is blocked by an upper half portion of an isotropic optical lens 5020 for detection and a lower half portion of the isotropic optical lens 5020 is used as an aperture thereof, the aperture angle in the two directions perpendicular to each other can be changed, resulting in improvement of an effect to change an intensity ratio of a signal coming from a defect to a background signal. This can achieve an increase in sensitivity for detection of the defect.

In addition, the upward detection optics system and the oblique detection optics system can be installed at positions different from each other to achieve the best detection performance, respectively.

Figure 13:
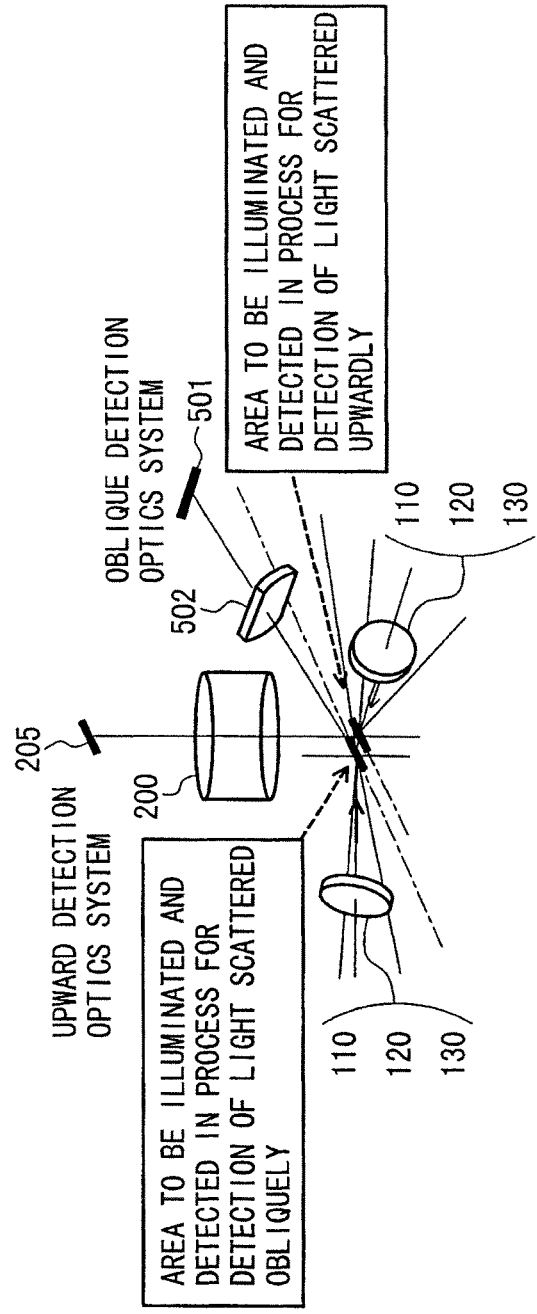
FIG. 13 is a diagram showing another example of the modification of the present invention.

When the upward detection optics system and the oblique detection optics system are used to improve the sensitivity for detection of the defect, the two optics systems preferably measure the same location simultaneously to reduce a throughput time. In this case, the conditions for irradiation of the illumination light beam, such as an elevation angle, an azimuth angle, and polarization conditions, are limited to a single type of the conditions. There are many cases where the optimal conditions for illumination vary depending on the defect to be detected and on the combination of the upward detection optics system and the oblique detection optics system. It is necessary to change illumination conditions for each of the two optics systems in order to detect a defect with high sensitivity under the optimal conditions for irradiation of the illumination light beam by using the upward detection optics system and the oblique detection optics system. As shown in FIG. 13, each of the upward detection optics system and the oblique detection optics system simultaneously performs a single inspection under the illumination conditions for each of the upward detection optics system and the oblique detection optics system, the illumination conditions for the upward detection optics system being different from the illumination conditions for the oblique detection optics system. The simultaneous inspections performed by the two detection optics systems make it possible to detect a defect with high sensitivity. In this case, the two detection optics systems are installed at positions different from each other.

Figure 14:
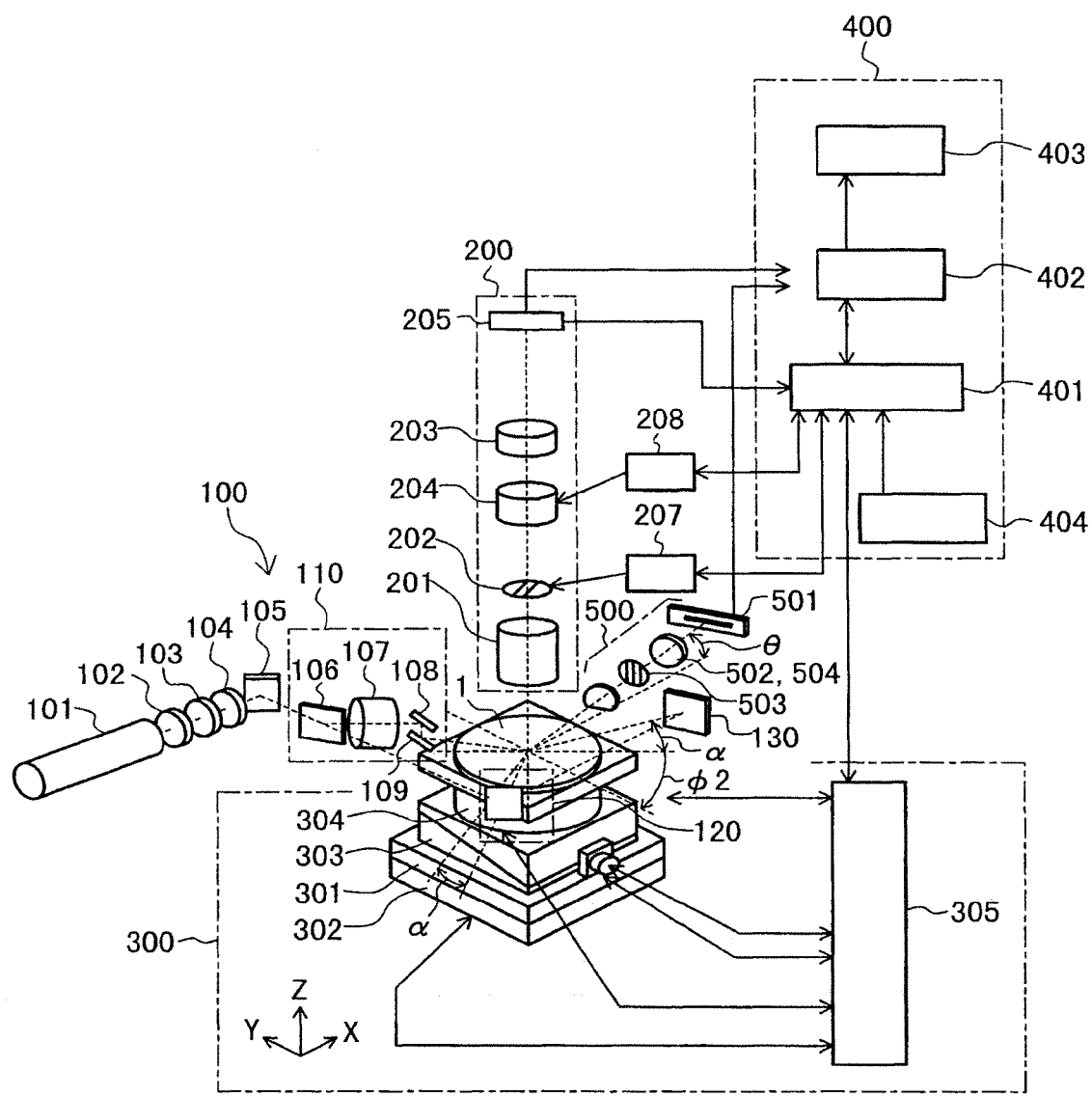
FIG. 14 is a diagram showing the configuration of a defect inspection system applied to the present invention.

FIG. 14 is a diagram showing the configuration of the defect inspection system applicable to the present invention. The defect inspection system shown in FIG. 14 includes a stage section 300, an optics system 100 for illumination, an optics system (hereinafter referred to as a "upward detection optics system") 200 for detection of light scattered upwardly with respect to the surface of a sample, an optics system (hereinafter referred to as a "oblique detection optics system") 500 for detection of light scattered obliquely with respect to the surface of the sample, and a control system 400. The stage section 300 is adapted to move a sample such as a wafer in an X-axis direction, Y-axis direction, and Z-axis direction and to rotate around the Z-axis. The optics system 100 is adapted to irradiate illumination light beam on the sample for detection of a defect. The upward detection optics system 200 is adapted to detect light reflected from the sample. The oblique detection optics system 500 is adapted to detect light reflected from the sample. The control system 400 is adapted to execute arithmetic processing, signal processing, and the like.

The stage section 300 has an X stage 301, a Y stage 302, a Z stage 303, a rotation stage 304, and a stage controller 305. The optics system 100 for illumination has a laser source 101, a beam expander composed of a concave lens 102 and a convex lens 103, a beam formation section composed of an optical filer group 104 and a mirror 105, and first, second and third beam spot imaging sections 110, 120 and 130. The first beam spot imaging section 110 includes an optical branching element (or a mirror) 106, an illumination lens 107 having a conic surface, and mirrors 108 and 109. The optical filter group 104 includes a neutral density (ND) filter and a wavelength plate.

As the laser source 101, a third-harmonic generation (THG) of a high power YAG laser is preferably used. The THG has a wavelength of 355 nm. It is not necessary that the THG necessarily have the wavelength of 355 nm. In addition, it is not necessary that the YAG laser and the THG are necessarily used as the laser source 101. Specifically, as the laser source 101, an Ar laser, a nitrogen laser, an He—Cd laser, an excimer laser, or the like may be used.

The upward detection optics system 200 has a detection lens 201, a space filter 202, an imaging lens 203, a zoom lens group 204, a one-dimensional detector (image sensor) 205, a space filter controller 207, and a zoom lens controller 208. The oblique detection optics system 500 has a one-dimensional detector (image sensor) 501, an objective lens 502, a space filter 503, and an imaging lens 504. The one-dimensional detector 205 may be a time delay integration (TDI) sensor. The control system 400 has an arithmetic processor 401, a signal processor 402, an output section 403, and an input section 404. The arithmetic processor 401 has a central processing unit (CPU) and the like and controls a driving system such as a motor, coordinates, and the sensors. The signal processor 402 has: an analog-digital converter, a data memory capable of delaying data, a differential processing circuit for calculating a difference between signals supplied from chips, a memory for temporarily storing a signal indicative of the difference between the signals supplied from the chips, a threshold calculator for setting a pattern threshold, comparator, and the like.

The output section 403 is adapted to store a result of detection of a defect such as a foreign material and to output or display the result of detection of the defect. The input section 404 is adapted to input a command and data to the arithmetic processor 401 in accordance with an operation performed by a user. A system of coordinates is shown at the lower left of FIG. 14. In FIG. 14, an X axis and a Y axis are plotted in a horizontal plane, and a Z axis is plotted in a vertical direction. The horizontal plane is parallel to the surface of the sample, and the vertical direction is perpendicular to the surface of the sample. The upward detection optics system 200 has an optical axis parallel to the Z axis, and the oblique detection optics system 500 has an optical axis parallel to the horizontal plane xz.

Figure 15:
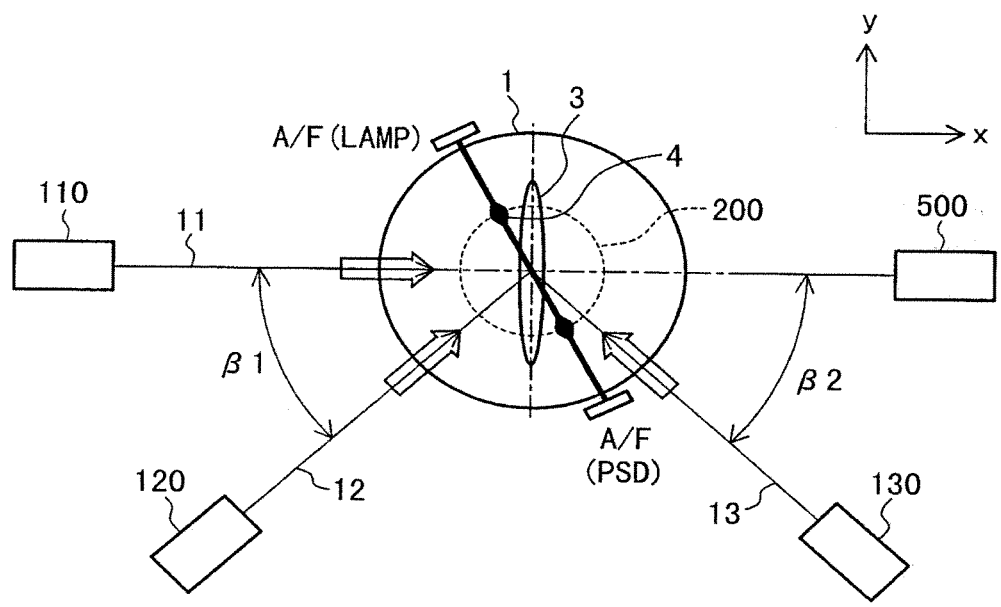
FIG. 15 is a diagram showing three beam spot imaging sections of the optics system for illumination.

The three beam spot imaging sections 110, 120 and 130 of the optics system 100 for illumination will be described with reference to FIGS. 15 and 16. FIG. 15 is a top view of a sample 1 which is a wafer. In FIG. 15, an illumination light beam 11 is irradiated on the surface of the sample 1 from the X-axis direction through the first beam spot imaging section 110. An illumination light beam 12 is irradiated on the surface of the sample 1 from a direction inclined at an angle of 45 degrees with respect to the Y-axis direction in the horizontal plane through the second beam spot imaging section 120, and an illumination light beam 13 is irradiated from a direction inclined at an angle of 45 degrees with respect to the Y-axis direction and perpendicular to the direction of traveling of the illumination light beam 12 in the horizontal plane through the third beam spot imaging section 130. The oblique detection optics system 500 is installed at a position on the opposite side of the first beam spot imaging section 110 with respect to the sample 1.

The illumination light beams 11, 12 and 13 are irradiated on the surface of the sample 1 at a predetermined elevation angle α with respect to the surface of the sample 1. In particular, the elevation angle α of the illumination light beams 12 and 13 can be reduced to decrease the amount of light to be detected scattered from the bottom surface of a thin transparent film. The illumination light beams 11, 12 and 13 form an elongated beam spot 3 on the sample 1. The length of the beam spot 3 is extended in the Y-axis direction, and is larger than a diameter of a light receiving area 4 of the one-dimensional detector 205 provided in the upward detection optics system 200. A description will be made of the reason for installations of the three beam spot imaging sections 110, 120 and 130 in the optics system 100 for illumination. When an angle formed between the direction of traveling of the illumination light beam 11 and the direction of traveling of the illumination light beam 12 in the horizontal plane is β1, and an angle formed between the direction of traveling of the illumination light beam 13 and the X-axis direction is β2, β1=β2=45 degrees in the embodiment of the present invention. This arrangement makes it possible to prevent light diffracted in zero order from a non-repetitive pattern on a substrate of the sample 1 from being incident on the objective lens 201 of the upward detection optics system 200.

The non-repetitive pattern on the substrate of the sample 1 is mainly composed of linear patterns each having lines, which are parallel or perpendicular to the lines of another one of the linear patterns. The lines of each of the linear patterns are parallel to the X-axis direction or the Y-axis direction. The pattern formed on the substrate of the sample 1 projects, and a recessed portion is formed between the adjacent linear patterns. The illumination light beams 12 and 13 emitted from directions inclined at an angle of 45 degrees with respect to the X and Y axes are blocked by the circuit pattern which projects, and cannot be irradiated on the recessed portion formed between the linear patterns. The beam spot imaging section 110 is provided on the X axis to emit the illumination light beam 12 for detection of a defect. Thus, the illumination light beam 11 can be irradiated on the recessed portion between the adjacent linear patterns to detect a defect such as a foreign material present on the recessed portion. The sample may be rotated by 90 degrees based on the direction of the lines of the linear pattern to ensure that the sample is inspected. Alternatively, the illumination light beam 11 may be irradiated on the sample from the Y-axis direction to inspect the sample. When the illumination light beam is irradiated on the sample in the X-axis direction, i.e., on the recessed portion formed between the adjacent linear patterns as is the illumination light beam 11, it is necessary that the detector block zero-order diffracted light to ensure not to detect the zero-order diffracted light. To block the zero-order diffracted light, the space filter 202 is provided.

Figure 16A:
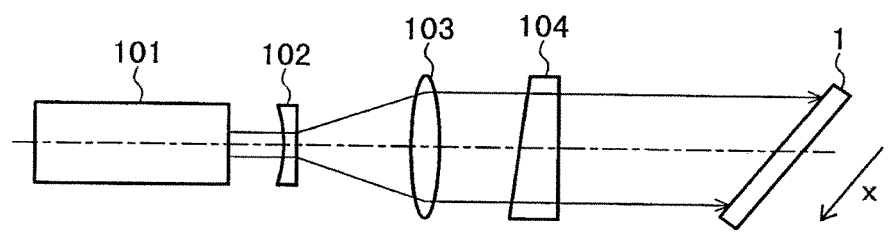
FIGS. 16A and 16B are each a diagram explaining a method for forming an elongated beam spot.
Figure 16B:
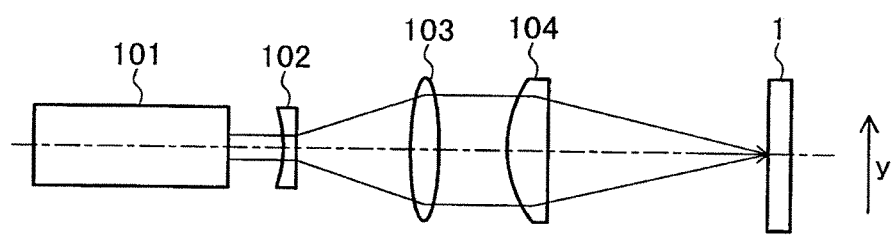

Next, with reference to FIGS. 16A, 16B and 17, a method for forming an elongated beam spot 3 will be described. Each of FIGS. 16A and 16B shows the laser source 101, the concave lens 102, the convex lens 103 and the illumination lens 104, which are provided in the optics system 100 for illumination. The other elements 105, 106, 107, 108, and 109 of the optics system 100 are omitted in FIGS. 16A and 16B. The illumination lens 104 is cylindrical, that is, has a conic shape. As shown in FIG. 16A, the focal length of the illumination lens 104 is linearly varied in a longitudinal direction thereof. As shown in FIG. 16B, the illumination lens 104 has a cross section of the shape of a flat convex lens.

Figure 17:
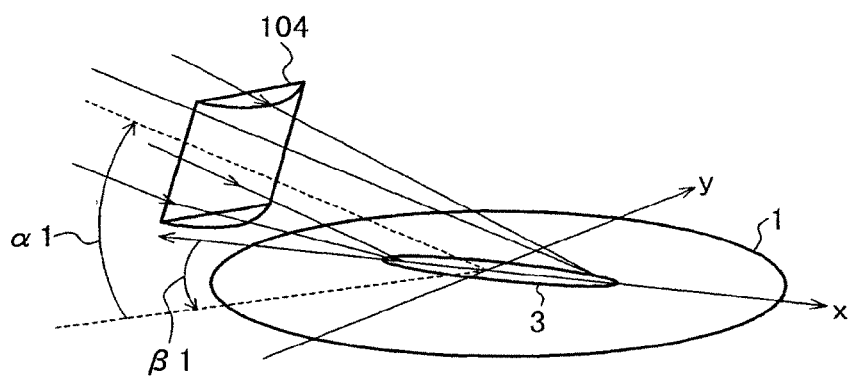
FIG. 17 is a diagram explaining the method for forming the elongated beam spot.

As shown in FIG. 17, the illumination light beam is incident on the sample 1 at an elevation angle α1 with respect to the surface of the sample 1 with a reduction in the aperture of the illumination lens in the Y-axis direction, the illumination light beam being collimated in the X-axis direction. The illumination light beam forms an elongated beam spot 3 on the surface of the sample 1. In FIG. 17, an angle of the illumination light beam with respect to the surface of the sample 1 is α1 and an image of the illumination light beam irradiated on the sample 1 is formed in a direction inclined at an angle of β1 with respect to the X-axis direction. The use of the illumination lens 104 makes it possible to collimate the illumination light beam in the X-axis direction and to form the image of the illumination light beam in the direction inclined at the angle of β1, which is approximately 45 degrees, with respect to the X-axis direction.

Figure 18:
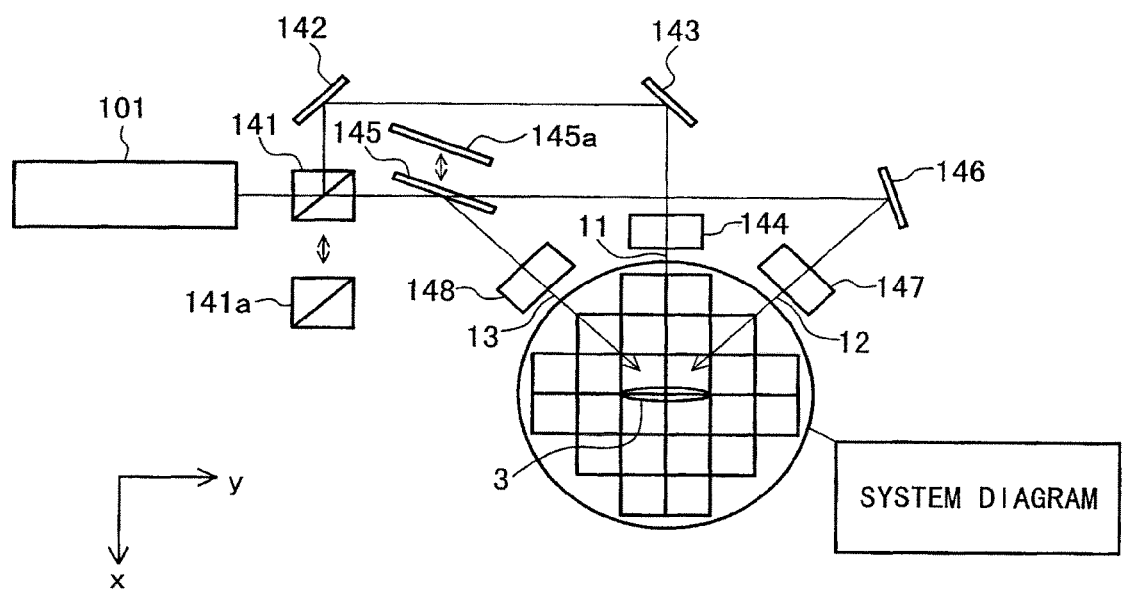
FIG. 18 is a diagram showing an example of the arrangement of three beam spot imaging sections provided in the optics system for illumination.

Next, a description will be made of an example of the configuration of the three beam spot imaging sections 110, 120 and 130 in the optics system 100 for illumination with reference to FIG. 18. In FIG. 18, the laser source 101 emits a laser beam, which is divided into two light beams by a first optical element 141 for branching of light such as half mirror. One of the light beams is reflected by a mirror 142 and a mirror 143 and incident on a concave lens 144 constituting the first beam spot imaging section 110. In this way, the illumination light beam 11 is generated by the first beam spot imaging section 110.

The other one of the light beams is divided into two light sub-beams by a second optical element 145 for branching of light such as a half mirror, the light sub-beams directing to light paths different from each other. One of the light sub-beams is reflected by a mirror 146 and incident on a concave lens 147 constituting the second beam spot imaging section 120. In this way, illumination light beam 12 is generated by the second beam spot imaging section 120. The other one of the light sub-beams is incident on a concave lens 148 constituting the third beam spot imaging section 130. In this way, illumination light beam 13 is generated by the third beam spot imaging section 130.

When the first optical element 141 is removed from the light path or replaced with an optical element 141a, which passes light without reflecting and branching the light, the illumination light beam 11 is not generated by the first beam spot imaging section 110. That is, the illumination light beam 12 and the illumination light beam 13 are only generated by the second beam spot imaging section 120 and the third beam spot imaging section 130, respectively. In addition, when the first optical element 141 is removed from the light path or replaced with the optical element 141a, and the second optical element 145 is replaced with a mirror 145a for reflecting light without passing and branching the light, the illumination light beam 13 is only generated by the third beam spot imaging section 130.

When the first optical element 141 is removed from the light path or replaced with the optical element 141a, and the second optical element 145 is removed from the light path or replaced with an optical element, which passes light without reflecting and branching the light, the illumination light beam 12 is only generated by the second beam spot imaging section 120. When the first optical element 141 is installed and the second optical element 145 is replaced with the mirror 145a, the illumination light beam 11 and the illumination light beam 13 are only generated by the first beam spot imaging section 110 and the third beam spot imaging section 130, respectively.

When the first optical element 141 is installed, and the second optical element 145 is removed or replaced with the optical element, which passes light without branching and reflecting the light, the illumination light beam 11 and the illumination light beam 12 are only generated by the first beam spot imaging section 110 and the second beam spot imaging section 120, respectively. As described above, the illumination light beams 11, 12 and 13 can be selectively generated by the three beam spot imaging sections 110, 120 and 130.

Figure 19:
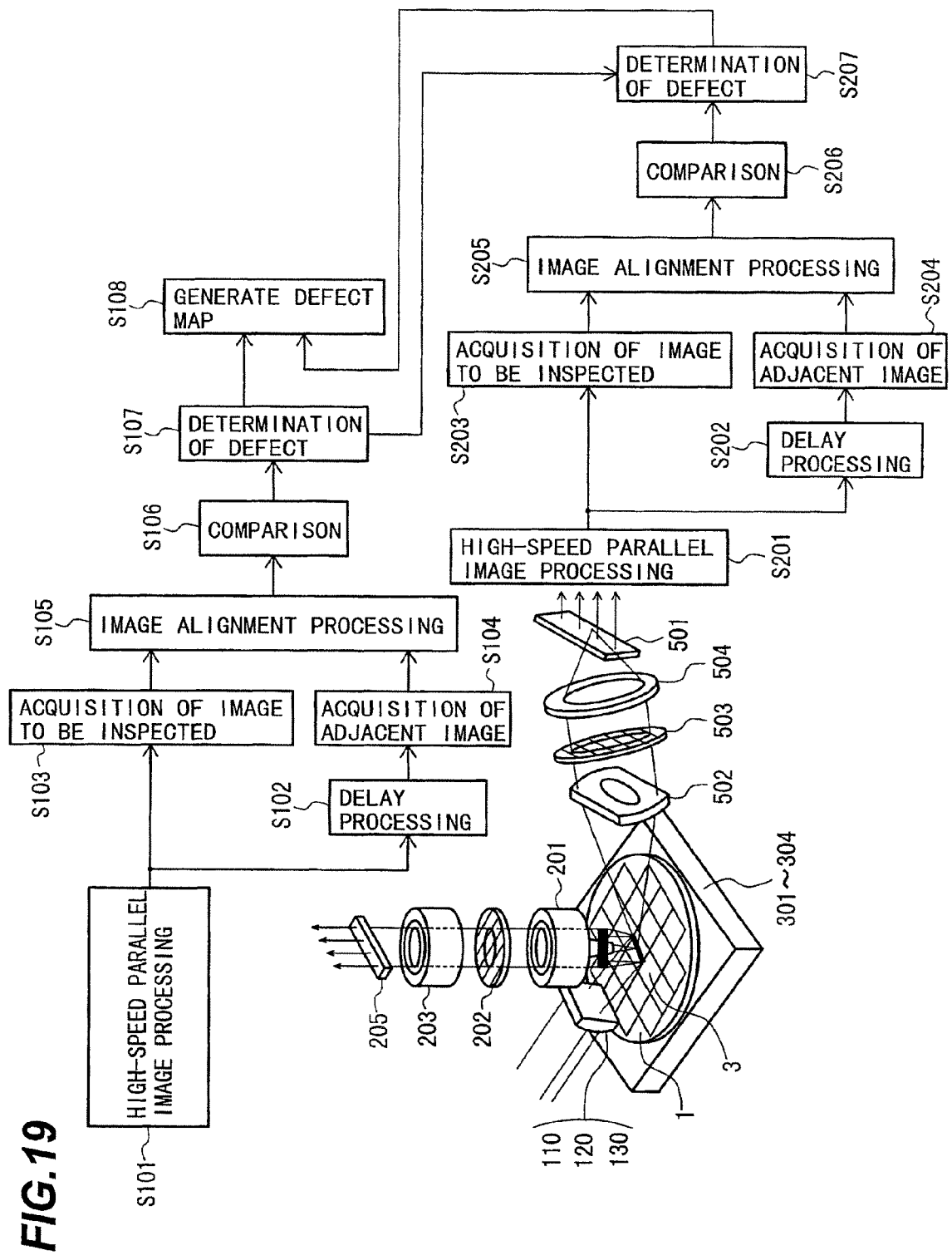
FIG. 19 is a diagram showing an optics system for detection of light scattered upwardly with respect to the surface of the sample.

Next, with reference to FIG. 19, a description will be made of the upward detection optics system 200. In FIG. 19, the illumination light beam is irradiated on the sample 1 to form an elongated beam spot 3, and reflected by and scattered from the sample 1. The light is output from upper and bottom surfaces of the transparent thin film, a circuit pattern present on the substrate of the sample 1, and a defect such as a foreign material. The output light is received by the detector 205 via the detection lens 201, the space filter 202 and the imaging lens 203 included in the upward detection optics system 200, and photoelectrically converted by the detector 205. Since the illumination intensity (power) of flux of light emitted from the laser source 101 can be controlled by the ND filter of the optical filter group 104 or by controlling laser power, a dynamic range of output of the detector 205 can be controlled.

Next, the space filter 202 will be described. The illumination light beam is irradiated on the repetitive pattern present on the sample 1 to form an interference fringe of diffracted light. When the detector 205 receives the interference fringe of diffracted light, an error signal is generated. In this case, the detector 205 cannot detect a defect such as a foreign material. The space filter 202 is arranged in a spatial frequency domain of the objective lens 201, i.e., at a location (corresponding to an exit pupil) of a Fourier-transformed image in order to block the Fourier-transformed image based on the light diffracted by the repetitive pattern.

As described above with reference to FIGS. 5A and 5B, the chip formed on the wafer includes a repetitive pattern, a non-repetitive pattern, and a part not having a pattern in general. The line width of the repetitive pattern is varied depending on the circuit pattern. It is general that as the space filter 202, a light blocking pattern is set to block light frequently diffracted by the repetitive pattern. As the space filter 202, the light blocking pattern may be changed. Alternatively, as the space filter 202, a plurality of light blocking patterns different from each other may be provided. In any of the above cases, the light blocking pattern may be changed or replaced based on the circuit pattern to block the diffracted light.

As described above, when the illumination light beam 11 is irradiated on the recessed portion between the linear patterns in the X-axis direction, it is necessary that zero-order diffracted light be blocked by the space filter 202. It is preferable that the space filter 202 be installed to block not only the zero-order diffracted light but also high-order diffracted light.

Next, a description will be made of a method for adjusting detection sensitivity based on the size of a defect such as a foreign material, which is to be detected. When the size of each of pixels of the one-dimensional detector (image sensor) 205, such as the TDI sensor, is reduced, the detector 205 can detect a smaller defect such as a foreign material although the throughput of the detector 205 is reduced, the size of each of the pixels being measured based on an image formed on the sample 1 by the pixels of the detector 205. In order to vary the size of the image formed on the sample 1 by the pixels of the one-dimensional detector (image sensor) 205, three types of the upward detection optics systems 200 are prepared.

To detect a defect such as a foreign material, having a length or a diameter of 0.1 μm or less, the upward detection optics system 200 having a small pixel size measured based on an image formed on the sample 1 by the pixels thereof is selected for use. Lenses of the zoom lens group 204 may be selected to ensure that the configuration of the upward detection optics system 200 having the small pixel size is achieved. For example, the configuration of the lenses of the zoom lens group 204 may be designed to ensure that the length of a light path from the sample 1 to the one-dimensional detector 205 such as the TDI sensor is not varied. If it is difficult to achieve the configuration of the zoom lens group 204, a mechanism for controlling the distance between the sample 1 and the one-dimensional detector 205 (image sensor) may be used in addition to the selection of the lenses of the zoom lens group 204. In addition, the one-dimensional detector 205 having a different pixel size may be used.

Next, a description will be made of the oblique detection optics system 500 with reference to FIG. 19. The optical axis of the oblique detection optics system 500 is inclined at a predetermined angle β with respect to the surface of the sample 1. To reduce the amount of light which is scattered from the bottom surface of the transparent thin film and detected, the optical axis of the oblique detection optics system 500 needs to be set to ensure that light output at angles from 80 to 90 degrees with respect to the surface of the sample 1 is detected. The adjusted elliptical lens 502 according to the present invention can be used to ensure that the oblique detection optics system 500 is installed at a position corresponding to a low elevation angle with respect to the surface of the sample 1. Light reflected from the elongated beam spot formed on the sample 1 is detected by the one-dimensional detector (image sensor) 501 via the objective lens 502, the space filter 503 and the imaging lens 504.

In the example shown in FIG. 19, the one-dimensional detector (image sensor) 501 is used to detect an image of the elongated beam spot. The space filter 503 is adapted to block an interference fringe of light diffracted from the repetitive pattern present on the sample in the same manner as the space filter 202.

The outline of a method for detecting a defect such as a foreign material will be described. In step S101 shown in FIG. 19, the control system receives a signal from the one-dimensional detector (image sensor) 205 of the upward detection optics system 200 to execute high-speed parallel image processing on the received signal. In step S103, the control system acquires an image to be inspected. In step S104, the control system acquires an image adjacent to the image to be inspected after delay processing in step S102. Next, in step S105, the control system executes image alignment processing to align the image to be inspected and the adjacent image.

Then, in step S106, the control system compares the image to be inspected with the adjacent image.

In step S107, the control system determines a defect based on the result of the comparison. In step S201, the control system receives a signal from the one-dimensional detector (image sensor) 501 of the oblique detection optics system 500 to execute high-speed parallel image processing on the received signal. Steps S202 to S207 are the same as step S102 to S107. The control system combines information on the defect based on the result of the determination in step S107 with information on the defect based on the result of the determination in step S207 to make a comprehensive determination. Lastly, in step S108, the control system combines the defect detected by the upward detection optics system 200 with the defect detected by the oblique detection optics system 500 to generate a defect map.

In the example shown in FIG. 19, the defect inspection system performs the defect determination in step S107 and the defect determination in step S207. The defect inspection system may perform both defect determinations in a single step to generate a defect map.

Specifically, as shown in FIG. 20, the control system may compare the result of the comparison in step S106 with the result of the comparison in step S206 to perform the comprehensive determination in step S107, and then generate a defect map in step S108.

Next, a description will be made of the case where the defect inspection system according to the present invention inspects a defect under a plurality of conditions. The inspection is performed for the purpose of increasing the dynamic range, for example. Three conditions are set based on power (high power, medium power, and low power) of the illumination light. The three conditions correspond to a priority on an area, a standard, and a priority on sensitivity.

Under the three conditions, the defect inspection system inspects the surface of the wafer, which is the sample, and combines results of the inspections to generate an inspection result map (which is a drawing in which a mark indicative of a defect such as a foreign material detected from the sample 1 is plotted on position coordinates). The inspection result map may be replaced with a coordinates list of defects, or a list or map expressing levels of detection signals obtained from defects. The defect inspection system performs the inspection for the purpose of detecting a more microscopic scratch or defect such as a foreign material, in addition to the purpose of increasing the dynamic range. In this case, conditions for the inspection includes scanning time of each of the stages 301 and 302, angles α1, β1 (including a value of zero) and β2 (including a value of zero) of the illumination light beam generated by the optics system 100, and the presence of the wavelength plate 104, and the like.

Next, a description will be made of a production line and a production method for manufacturing a semiconductor and the like by using the defect inspection system according to the present invention. The semiconductor production line using the defect inspection system according to the present invention includes a manufacturing process, a probe inspection process, an inspection system and a data analysis system. The manufacturing process, especially, a process affecting the yield is always monitored by the inspection system including the defect inspection system according to the present invention. When any abnormality in the processes is detected by the monitoring performed by the inspection system, the process or the system, which causes the abnormality, is identified by the inspection system.

In order to inspect a foreign material or a defect such as a foreign material attached to a top surface of the sample in a desired process with high accuracy of identification, it is preferable that the defect inspection system according to the present invention perform the inspection of a defect such as a foreign material before and after the desired process to calculate a logical difference between a result of the defect inspection after the desired process and a result of the defect inspection before the desired process.

It is not always that only a defect such as a foreign material occurring in the desired process can be detected based on the logical difference. The reason is described as follows. For example, a film is formed on the surface of the defect such as a foreign material in a film formation process or the like, resulting in an increase in the size of the defect. This improves inspection sensitivity. As a result, a defect present before the film formation process is inspected after the film formation process. More specifically, the defect present before the film formation process is not inspected before the film formation process and is inspected after the film formation process, resulting in the fact that it is mistakenly determined that the defect occurs in the film formation process.

In the defect inspection system according to the present invention, however, the oblique detection optics system can be installed at a position corresponding to a low elevation angle and is capable of detecting only a defect present on the surface of the sample with a reduction in the amount of light scattered from a background defect. This makes it possible to eliminate an incorrect determination.

As described above, the defect inspection system according to the present invention is capable of improving the efficiency of illumination. Also, the defect inspection system is capable of detecting, with high sensitivity, a foreign material present on the surface such as a LSI pattern by using the space filter and optimizing the angle of the traveling direction of the illumination light with respect to the surface of the sample. In addition, the defect inspection system is capable of reducing light diffracted from a pattern present on the substrate. Furthermore, the defect inspection system is capable of setting a low detection threshold for separating background light from light which is reflected on a foreign material present on the surface of the sample and is detected, in order to avoid an effect of an increase and reduction in the amount of light due to thin film interference of diffracted light caused by a variation in the thickness of the transparent thin film.

Thus, the defect inspection system is capable of detecting a microscopic foreign material present on the surface of the sample having a length or diameter of about 0.1 μm with high sensitivity and preventing incorrect detection.

In the defect inspection system according to the present invention, light scattered from a foreign material present on the surface of the substrate and light scattered from an internal pattern can be separated from each other. The defect inspection system performs the inspection for each process for producing a wafer to determine a process causing a foreign material, making it possible to quickly identify a source of the defect.

In addition, the defect inspection system according to the present invention is capable of simultaneously obtaining outputs from the detector of the upward detection optics system and from the detector of the oblique detection optics system in a single inspection to obtain the double of the amount of information compared with conventional techniques. This makes it possible to reduce the throughput time by half.

Furthermore, the defect inspection system according to the present invention has a plurality of the detectors capable of detecting light scattered from a foreign material in a direction different from that of light to be detected by the conventional techniques. Since the defect inspection system can obtain the double of the amount of information and the double of the value of the information, the defect inspection system can determine the size and the shape of the foreign material more accurately than the conventional techniques.

It should be noted that, as shown in FIG. 7B, a plurality of the adjusted elliptical lenses 10B can be installed in the same optical axis thereof to correct aberration. In this case, when the elevation angle is 12 degrees, seven to fifteen of the adjusted elliptical lenses can be installed.

What is claimed is:

1. An inspection apparatus comprising:
   an illumination system which supplies an object with light, and forms a substantive illuminated line on said object;
   a detection system which collects light from said line, wherein:
   said detection system includes a plurality of lenses,
   said lenses are stacked along an optical axis of said detection system,
   said plurality of lenses includes at least an objective lens that is a substantially ellipsoidal lens, and
   the inspection apparatus further comprises another detection system which includes a substantially ellipsoidal objective lens, the substantive illuminated line is formed between the detection system and the another detection system when the object is seen from an upper part of the object.

2. The inspection apparatus according to claim 1, wherein each lens is a substantially ellipsoidal lens.

3. The inspection apparatus according to claim 2, further comprising an image sensor for detecting the collected light and generating an image.

4. The inspection apparatus according to claim 3, further comprising a processing system for high speed parallel image processing said image.

5. The inspection apparatus according to claim 4, wherein said processing system acquires a first image of a first predetermined area on said object and a second image of a second predetermined area adjacent to said first predetermined area, substantially coincides a position of said first image with a position of said second image, and detects an anomaly of said object.

6. The inspection apparatus according claim 5, further comprising another detection system which includes a substantially ellipsoidal objective lens, the substantive illuminated line is formed between the detection system and the another detection system when the object is seen from an upper part of the object.

* * * * *